(12) United States Patent
Roesler et al.

(10) Patent No.: US 11,267,627 B2
(45) Date of Patent: Mar. 8, 2022

(54) MEDICAL PACKAGING WITH A PACKAGING SLEEVE AND OUTER VACUUM PACKAGING

(71) Applicants: Peter Roesler, Wangen (DE); Thiemo Roesler, Wangen (DE)

(72) Inventors: Peter Roesler, Wangen (DE); Thiemo Roesler, Wangen (DE)

(73) Assignee: ROESLER IP GMBH

( * ) Notice: Subject to any disclaimer, the term of this patent is extended or adjusted under 35 U.S.C. 154(b) by 129 days.

(21) Appl. No.: 16/129,074

(22) Filed: Sep. 12, 2018

(65) Prior Publication Data
US 2019/0077563 A1    Mar. 14, 2019

(30) Foreign Application Priority Data

Sep. 14, 2017    (DE) .......................... 102017121374.0

(51) Int. Cl.
*B65D 75/12*    (2006.01)
*A61B 50/30*    (2016.01)
(Continued)

(52) U.S. Cl.
CPC .............. *B65D 75/12* (2013.01); *A61B 50/30* (2016.02); *B65D 75/26* (2013.01);
(Continued)

(58) Field of Classification Search
CPC ...... B65D 75/12; B65D 75/30; B65D 75/305; B65D 75/38; B65D 3/20; B65D 59/04;
(Continued)

(56) References Cited

U.S. PATENT DOCUMENTS 2,549,039 A * 4/1951 Adams ............. A61B 17/06128
                                                          206/63.3
3,095,972 A * 7/1963 Sorenson ............... A61B 50/30
                                                            206/365

(Continued)

FOREIGN PATENT DOCUMENTS

| DE | 10301449 | 7/2004 |
|---|---|---|
| DE | 60222726 | 7/2008 |
| DE | 102009013947 | 9/2010 |
| EP | 1870340 | 12/2007 |
| EP | 2108381 | 10/2009 |
| WO | 2002038360 | 5/2002 |

*Primary Examiner* — Robert Poon
(74) *Attorney, Agent, or Firm* — Dentons Cohen & Grigsby P.C.

(57) ABSTRACT

Medical packaging for the sterile storage of medical articles in a hermetically and sterile sealable packaging sleeve. The packing generally includes at least two parts, with a sealed, film-like outer packaging, which at least partially encloses the packaging sleeve in a form-fitting manner and provides a pressure that is reduced with respect to the atmosphere. At least one end face of the packaging sleeve may be designed to be flattened, wherein a length of the outer packaging is generally longer than a length of the packaging sleeve and projects beyond the end face region of the packaging sleeve. A sealing or welding seam may be arranged at least in the end face region of the packaging sleeve, wherein at least one of the end faces of the packaging sleeve, preferably both end faces, are designed so as to be flattened off. The end-sided transition from the packaging sleeve into the outer packaging is substantially wrinkle free.

20 Claims, 6 Drawing Sheets

(51) Int. Cl.
- *B65D 75/26* (2006.01)
- *B65D 75/58* (2006.01)
- *A61B 50/00* (2016.01)
- *A61B 90/00* (2016.01)
- *A61B 17/00* (2006.01)
- *A61B 17/86* (2006.01)
- *A61M 5/00* (2006.01)
- *B65D 33/00* (2006.01)
- *B65D 35/08* (2006.01)

(52) U.S. Cl.
CPC ........ *B65D 75/5855* (2013.01); *A61B 17/865* (2013.01); *A61B 2017/00526* (2013.01); *A61B 2050/006* (2016.02); *A61B 2050/0065* (2016.02); *A61B 2050/0086* (2016.02); *A61B 2050/314* (2016.02); *A61B 2090/037* (2016.02); *A61M 5/002* (2013.01); *B65D 33/007* (2013.01); *B65D 35/08* (2013.01); *B65D 2301/20* (2013.01)

(58) Field of Classification Search
CPC .......... B65D 59/00; B65D 59/06; B65D 1/32; B65D 1/095; B65D 35/10; B65D 1/09; B65D 65/04
USPC ..................................... 206/438; 220/8, 4.21
See application file for complete search history.

(56) References Cited

U.S. PATENT DOCUMENTS

| | | | | |
|---|---|---|---|---|
| 3,473,650 | A * | 10/1969 | Hoag | B65D 83/06 |
| | | | | 383/200 |
| 4,603,538 | A | 8/1986 | Shave | |
| 5,551,557 | A * | 9/1996 | Brooks | B65D 81/266 |
| | | | | 206/204 |
| 6,547,094 | B1 | 4/2003 | Jacobs | |
| 7,040,485 | B2 * | 5/2006 | Gupta | A61L 2/07 |
| | | | | 206/438 |
| 7,631,760 | B2 * | 12/2009 | Guelzow | A61F 2/0095 |
| | | | | 206/204 |
| 9,517,298 | B2 * | 12/2016 | Banik | A61B 17/06128 |
| 2006/0260967 | A1 * | 11/2006 | Clarke | A61F 2/0095 |
| | | | | 206/438 |
| 2008/0116106 | A1 | 5/2008 | Lampropoulos | |
| 2009/0314676 | A1 * | 12/2009 | Peck | B65D 33/01 |
| | | | | 206/438 |
| 2010/0288770 | A1 * | 11/2010 | Marco | B65D 75/5855 |
| | | | | 220/270 |
| 2012/0010552 | A1 * | 1/2012 | Greer, Jr | A61M 35/006 |
| | | | | 604/1 |
| 2012/0061274 | A1 * | 3/2012 | Tumminello | A61M 5/002 |
| | | | | 206/438 |
| 2012/0124943 | A1 * | 5/2012 | Nakamura | B65B 7/02 |
| | | | | 53/425 |
| 2016/0368679 | A1 * | 12/2016 | Roesler | B65D 85/12 |

\* cited by examiner

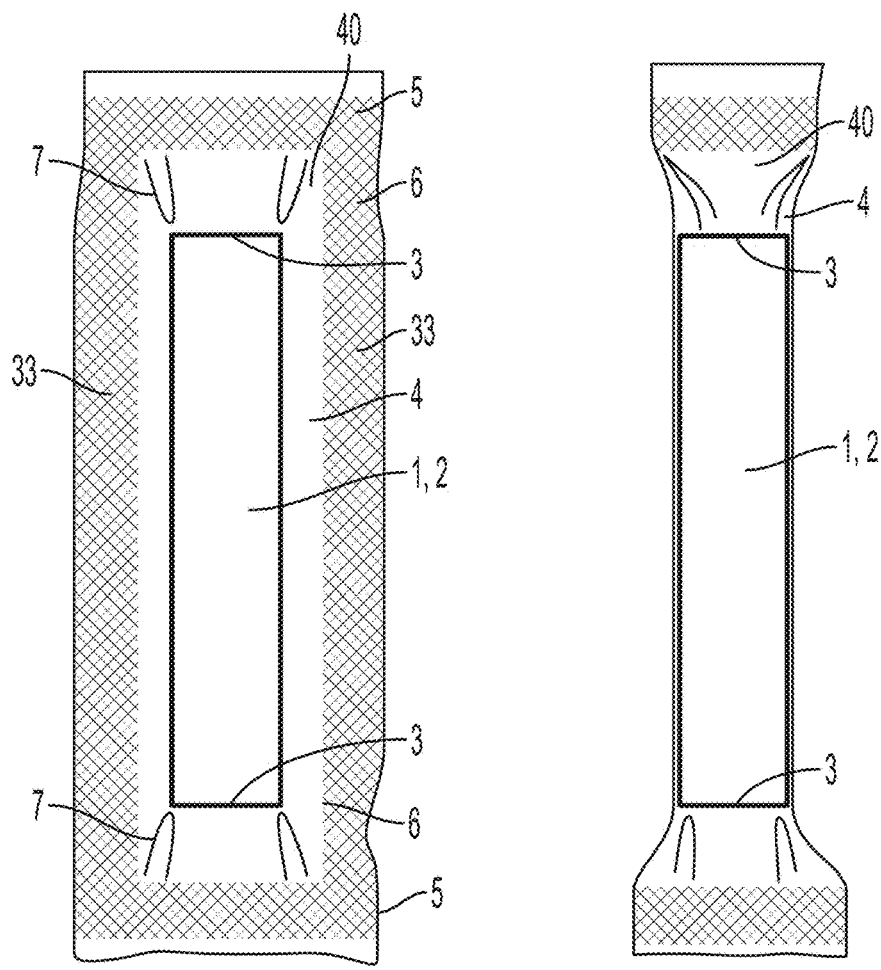
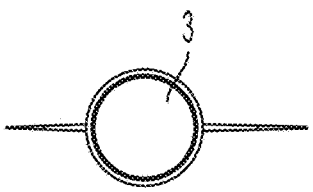
FIG. 1A
PRIOR ART
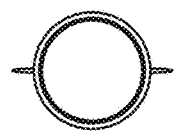
FIG. 2A
PRIOR ART
FIG. 1B
PRIOR ART
FIG. 2B
 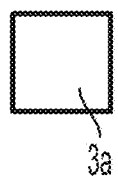 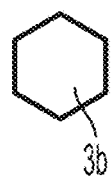
FIG. 3A  FIG. 3B  FIG. 3C

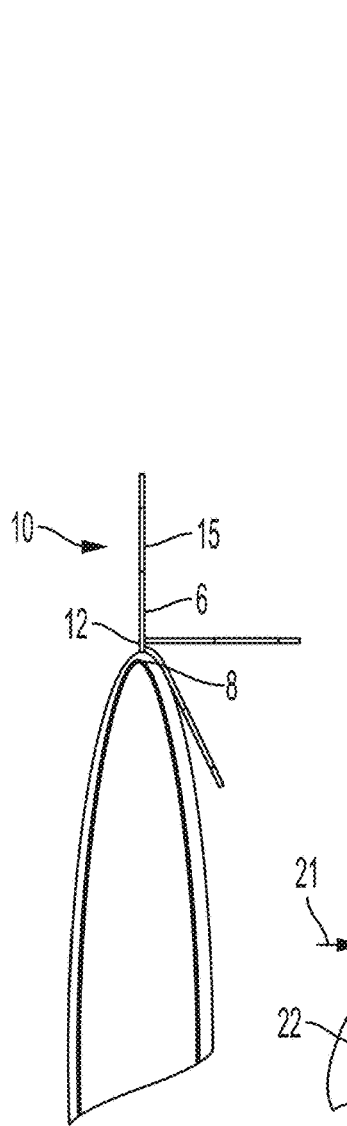 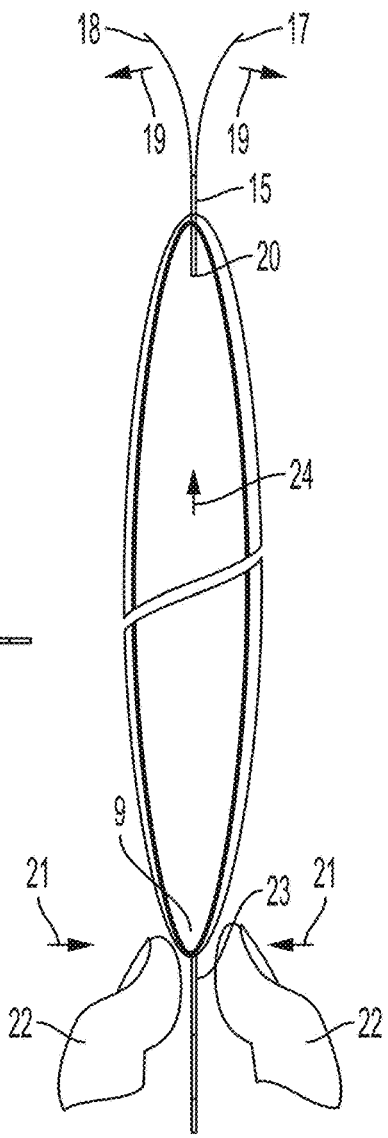 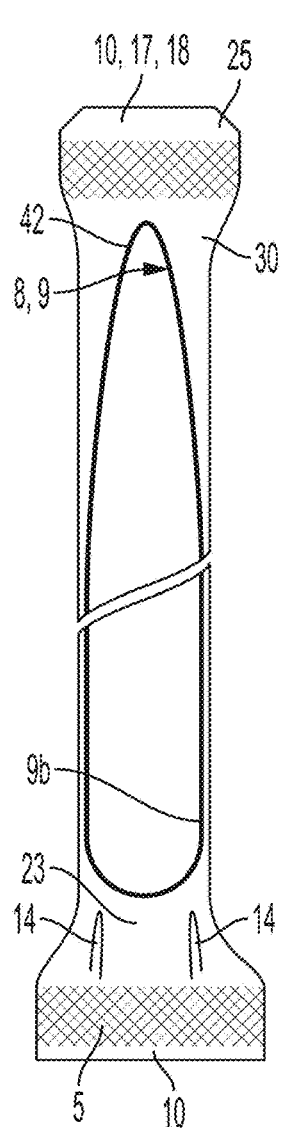
FIG. 10　　FIG. 11　　FIG. 12
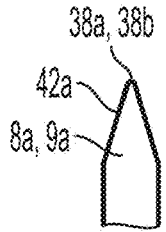 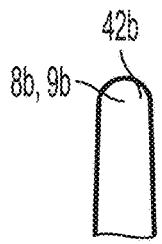 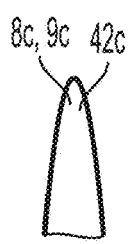 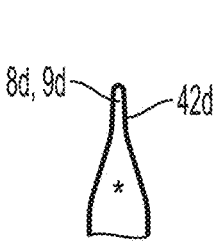
FIG. 13A　　FIG. 13B　　FIG. 13C　　FIG. 13D
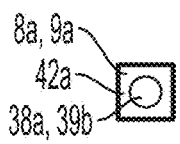 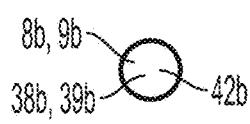 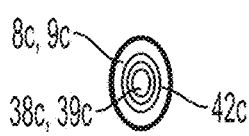 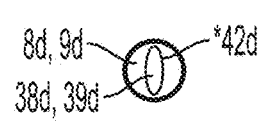
FIG. 13E　　FIG. 13F　　FIG. 13G　　FIG. 13H

MEDICAL PACKAGING WITH A PACKAGING SLEEVE AND OUTER VACUUM PACKAGING

CROSS REFERENCE TO RELATED APPLICATIONS

This application claims priority to German Patent Application DE 102017121374.0, filed Sep. 12, 2017, incorporated herein by reference.

FIELD OF THE INVENTION

The subject matter of the invention is a medical packaging sleeve for storing sterile medical articles with an outer packaging having an inner space with an air pressure that is reduced with respect to the atmosphere, with the goal that the outer packaging nestles as closely and as wrinkle free as possible against the packaging sleeve.

BACKGROUND OF THE INVENTION

The document DE 102009013947 A1 shows a packaging for packing pieces of packaged goods with a packaging sleeve that is formed to a multi-edged sleeve and which is surrounded by a shrink film. During thermal shrinkage of the shrink film, however, undesired wrinkles may form in the transition region between the shrink film and the end face of the multi-edge sleeve, so that if said wrinkles kink, the outer packaging may break open.

The documents EP 1870340 A1, U.S. Pat. No. 6,547,094 B1 and WO 200238360 A1 show a packaging sleeve in the manner of a hollow blown container having a lower end face that is flattened off. The flattening is due to the plastic tube being sealed off in order to close the container. The arrangement of an outer packaging is not provided.

The prior art also discloses cylindrical packaging sleeves, which usually consist of two sleeve parts, which, as a rule, can be inserted into one another and which accommodate any kind of article in the inner space. Such an article may be, for example, a drill, a milling machine, a sterile medical instrument or any other tool that is to be optimally protected against impact and shock.

It is known to design such a, typically two-piece, packaging sleeve such that it is designed so as to be approximately round cylindrical; and the ends of the two packaging sleeves, each facing in the opposite direction, are designed so as to be disk shaped. The result is that the packaging sleeves, which are part of the prior art, are flat and disk shaped on the end face. The plane of the disk-shaped, end-sided closure is perpendicular to the longitudinal center axis of the packaging sleeve.

Correspondingly it concerns blunt, end-sided ends of a known packaging sleeve. However, when said packaging sleeve is introduced into an outer packaging, which is then provided with a vacuum after the packaging sleeve has been introduced, said ends give rise to serious disadvantages.

When such a packaging sleeve is welded into an outer packaging while at the same time at least partially extracting the packaging air, wrinkles form in an undesired manner on the blunt-ended end faces in the outer packaging; and these wrinkles shorten the service life and reduce the tightness of the packaging.

It has been found that the undesired formation of wrinkles in the outer packaging results in the film material of the tubular film or the sheet film becoming brittle in the wrinkle region, when the said parts are bent, so that the formation of wrinkles causes predetermined breaking points to form in the film; and after prolonged use these predetermined breaking points result in the outer packaging breaking and, thus, lead to the loss of the protection and the sterilization of the packaging sleeve, received in the outer packaging.

The present invention is provided and is suitable preferably for the sterile packaging of medical surgical instruments, tools and implants. For this purpose there are particular requirements for the quality of the sealing, because air pockets in the area of the outer packaging at the packaging ends (also referred to as a "projecting length") have to be positively avoided. In contrast, when non-sterile foodstuffs or other articles of everyday use are packaged, such a formation of wrinkles is immaterial.

However, in the case of sterile packaging of surgical instruments and for articles that are necessary for the operation, such as screws, splints, artificial hip or knee joints or other implants and tools, it has been found that after a prolonged period of storage the undesired formation of wrinkles on the end faces of the packaging resulted in the sealing regions of the outer packaging, exhibiting the undesired wrinkles, becoming brittle.

In addition, it is customary to store the packagings, which have been produced in this way, in another outer packaging, such as, for example, a carton. However, the end-sided, sealed projecting lengths of the outer packaging are bent for purposes of better packaging.

This bending leads to the outer packaging being damaged in the region of the projecting lengths, if this region has undesired wrinkles, an aspect that in the event that medical articles are being packaged has to be avoided in any case.

At the same time it should be taken into account that such outer packagings and articles to be packaged have to be stable, according to the present invention, for a period of at least seven or eight years without incurring the risk that the packaging ends may break or separate unintentionally. However, the aforementioned formation of wrinkles leads to the material becoming brittle and, therefore, limits the service life of such a known packaging.

The subject matter of the document DE 10301449 A1 shows a sealed outer packaging for a medical article without the use of a packaging sleeve and with the depiction of the sealed end regions, which are to be avoided, according to the invention, and which show a significant formation of wrinkles.

The documents US 20120124943 A1 and U.S. Pat. No. 4,603,538 A1 show a packaging for medical articles. Said packaging consists of an outer, sealed packaging pouch having an inner space, in which there is disposed a second sealed packaging pouch, into which the medical article is inserted. However, there is no slightly bendable, mechanically stable packaging sleeve for both the storage of a medical article and for the air-free enclosure of the inner pouch by means of the outer pouch. The air-filled spaces, which are formed by the two packaging pouches, should be avoided. Such a packaging is not suitable for packaging articles with sharp edges. The packaged article is also not fixed in a positionally secure manner in such a packaging.

The document US 20080116106 A1 shows a deep-drawn packaging tray, which is made of a synthetic material and which is open upwards at one end. This packaging tray is intended for receiving medical articles in the manner of a packaging set having an opening that is sealed circumferentially with a cover film. As a result, said document does not show an individual packaging sleeve, which is present for each medical article and which is closed by an outer packaging that can be sealed. Upon opening the cover film, none of the packaged articles will be sterile any more. It is known to enclose such a packaging under vacuum in a sterile outer packaging pouch, as a result of which, double sterility is achieved. However, the drawback with this arrangement is that the inner packaging, which consists of the plastic tray with sharp edges, tends to push through the outer packaging pouch during transport, so that the sterility in the outer pouch is lost. There is an additional disadvantage that when a tubular outer pouch, which is closed and sealed under vacuum, is attached, an undesired formation of wrinkles is produced in the region of the packaging ends, because the contour of the packaging tray with edges is not adapted to the sealed projecting length.

The document EP 2 108 381 A1 shows in an analogous manner a deep-drawn packaging tray that is made of a synthetic material. This packaging tray is covered by two cover films, which are spaced the same distance apart from one another and accommodate a first medical article in their intermediate space, with the second article being placed in the packaging tray. The two cover films are sealed circumferentially onto the periphery of the rim of the carrier of the packaging tray. An individual packaging sleeve for an individual article, which is sterile packaged in said sleeve and which is protected against breakage in a positionally secured manner, is not apparent from this document. Therefore, such a packaging is suitable only for packaging soft medical articles, which do not have any edges, such as, for example, tubes. However, surgical tools, implants and tools, which have sharp edges and/or are heavy, cannot be sterile packaged in this way.

For this reason the goal of the present invention is to significantly extend the service life of packaging sleeves, which are packaged in a form-fitting manner with outer packagings, which can be sealed, and to avoid the formation of wrinkles in the region of the sealed end faces.

In particular, the objective is to significantly extend the service life of sterile packaged articles in a packaging sleeve that is surrounded in a form-fitting manner by a sealed outer packaging.

SUMMARY OF THE INVENTION

Therefore, the object of the present invention is to improve a packaging sleeve with an outer vacuum packaging in such a way that upon applying a vacuum in the outer packaging, a formation of wrinkles on the end faces of the packaging sleeve is largely avoided.

In order to achieve the aforementioned object, the invention is characterized by the technical teaching of claim 1.

A preferred embodiment provides a medical packaging for the sterile storage of medical articles in a hermetically sealable, sterile packaging sleeve, which consists of at least two parts and which comprises a sealed, film-like outer packaging that at least partially encloses the packaging sleeve in a form-fitting manner, wherein the outer packaging has a negative pressure that is reduced with respect to the atmosphere, 1. wherein at least one of the end faces of the packaging sleeve (1; 28, 29) is designed such that it is flattened,
2. wherein the length of the outer packaging (4) is longer than the length of the packaging sleeve and projects beyond the end face region of the packaging sleeve (1; 28, 29) and forms there a projecting length (10),
3. wherein the sealing or welding seam (5, 15) is arranged at least in the end face region of the packaging sleeve (1; 28, 29),
4. wherein at least one of the end faces of the packaging sleeve (1; 28, 29), preferably, however, both end faces form a streamlined profile, which passes from the larger periphery of the packaging sleeve into the sealed projecting length, which is narrow and reduced in thickness,
5. wherein the end-sided transition from the packaging sleeve into the outer packaging is substantially wrinkle free.

In a preferred embodiment it is provided that at least one of the end faces of the packaging sleeve, preferably, however, both end faces are designed so as to be flattened off and passes from the packaging sleeve, which is larger in diameter, into the flat, sealed projecting length of the outer packaging without wrinkles.

One advantageous feature is that now the end faces of the packaging sleeve are designed such that they are flattened in a streamlined shape, in particular, are designed like a beak or a pointed cone; and, as a result, the outer packaging, which surrounds the novel packaging sleeve on all sides in a form-fitting manner, enables a wrinkle-free, end-sided sealing of the packaging sleeve.

In this way it is possible to achieve an approximately continuous transition from the end faces of the packaging sleeve, said end faces being larger in diameter, into the form-fitting adjoining narrow regions of the outer packaging, with said regions being reduced in thickness, in the region of the sealed projecting length, because the tapering end faces of the packaging sleeve are adapted to the flat, sealed projecting length of the outer packaging.

Owing to this harmonic, mutual adaptation, small wrinkles with sharp edges and kinks in the sealed projecting length of the outer packaging are avoided. Instead, large transition radii, which flow into one another, are present in the transition region of the packaging sleeve into the projecting length, located on the outer pouch, an aspect that is achieved by the streamlined profile of the end faces of the packaging sleeve, with said streamlined profile tapering in the axial direction and decreasing conically in thickness.

As an analogous example from the fluid mechanics of flowing fluids, it could be said that the transition from the end face of the packaging sleeve into the end-sided adjoining, sealed projecting length of the outer pouch film should be shaped in a "streamlined" manner. For this reason the end faces of the packaging sleeve form a streamlined profile, which is enclosed by the outer packaging in a wrinkle free and form-fitting manner.

Consequently the sealing region of the outer packaging that is arranged on at least one end face—preferably, however, on both end faces—encloses the flattened end face region of the packaging sleeve in a harmonic, continuous and flowing manner and without wrinkles.

Said sealing region is designed such that it is preferably approximately flat, because the sealable outer packaging nestles against the end faces of the packaging sleeve in a form-fitting, seamless and wrinkle free manner, so that advantageously a wrinkle free sealing of the outer packaging in vacuo can take place, with the result that air pockets and an undesired formation of wrinkles are avoided.

That means that starting from an approximately round cylindrical or roughly similar cross section of the packaging sleeve, said cross section being predominant in the rest of the longitudinal region, the two opposite end faces of the respective sleeve parts are now no longer designed such that they are round cylindrical, but rather are flattened off. In a preferred embodiment the flattening is designed such that it is approximately beak shaped. It is preferred that the outer packaging in this end-sided region of the packaging sleeve be closed by an A-shaped or V-shaped seal.

In a first embodiment of such a packaging sleeve it concerns a single-sided or two-sided beak-shaped end, which corresponds in its width to approximately the diameter of the otherwise (approximately) cylindrical packaging sleeve, where in this case the beak-shaped end also tapers to a point in the view rotated by 90 degrees, in order to form in this way a flat end, which during vacuum packaging in an outer packaging no longer leads to the formation of wrinkles in the outer packaging in this region, because it adjoins in a harmonic flowing manner the sealed, flat projecting end of the outer packaging in the end face region.

Therefore, it is provided in accordance with the invention that the opposing end faces of a, moreover, cylindrical or approximately cylindrical packaging sleeve, which consists preferably of two sleeve parts that can be inserted or screwed into one another, are formed now as flat ends.

Instead of two, for example, identical sleeve parts, it is provided in another embodiment that a single sleeve part is used that is closed on an end face by means of a stopper that can be inserted or screwed.

Similarly it is provided in another embodiment to design the sleeve part so as to be open on both sides and to close each of the open end faces by means of a stopper that can be inserted or screwed.

Even in this case the shape of the end-sided stopper is to be adapted to the desired harmonic and continuous transition into the sealed or welded projecting length of the outer packaging. That means that the stopper is designed so as to be flat and/or beak shaped, in order to ensure in this way the wrinkle free transition into the outer packaging.

The packaging sleeve is made preferably of a transparent plastic material that exhibits such a flexural rigidity that the one packaging part can be slid onto the other packaging part such that it is stable to bending for purposes of closing the packaging. The flexural rigidity shall also be so high that in the event that the packaging falls down, the article, contained in the packaging, is protected against breakage; and the packaging itself is not damaged.

The term "outer packaging" is also defined, according to the invention, as a composite film in the manner of single layer or multi-layer packaging film, from which flexible packagings are made. The individual film layers are usually extruded or backed or, more specifically, laminated. The packagings are used mainly in the foodstuff industry.

The structure of this composite film consists of single layers, which are specified for the respective application. The assembly of the individual monofilms into a composite takes place by means of a solvent-free or also solvent-containing adhesive lamination. Extrusion lamination or even extrusion coating—even though less often now-a-days—is also used.

The carrier film is the film layer that is used for printing on the film. The composite film may be provided with an additional barrier layer, if the carrier film does not already have an adequate barrier of its own. Then the additional barrier layer can be introduced into the sealing film. Normally EVOH, embedded in PE, is used for this purpose.

Carrier films can also be provided with a small, medium and higher barrier. In the case of a two-layer composite one refers to a duplex; in the case of a three-layer composite one refers to triplex composite films. During thermoforming, the laminated composite films are used as the top film and less often as the bottom film. Composite films are also used as the tray sealing film for so-called tray sealers (sealed tray or pan). Composite films for tubular bag machines—horizontal and vertical—have already fulfilled their purpose for many years and, in particular, as tubular bag films.

Depending on the carrier, the composite films have a plethora of properties. The films can be made of polyester, cellulose film, aluminum as a barrier layer (impermeable layer), hydrophobized paper as the inside of butter wrap film, PA, PE, PP, or PETG.

The invention also relates to metallized films, which are produced, for example, on the basis of polypropylene by coating a carrier film in vacuum by vapor deposition with a very thin layer of (high purity) aluminum. This process is based on the physical gas phase deposition. In this way the films acquire a metallic luster. They can be laminated to other films. Last, but not least, this treatment is also carried out for the optical effect. On the other hand, the metallized variant offers protection against light and oxygen.

The term "outer packaging" is also defined in the context of the invention as a blown film, which includes films made of thermoplastics, which are manufactured with the aid of a blown film line.

In the case of blown films the tear propagation resistance in the longitudinal and transverse direction is very similar. There are films, which consist of only a single layer (so-called mono blown film), and films, which are made of a plurality of layers (so-called coextruded blown film). In the case of a coex blown film there is the possibility of combining the positive properties of various materials in one film. Thus, there is, for example, a packaging for hams that consists of five different layers:

1. outside: a printable layer, usually polypropylene or polyethylene
2. between the outside and the center: adhesion promoter made of ethylene vinyl alcohol or ethylene vinyl acetate
3. center: a barrier layer made of polyamide for "locking in" the aroma
4. between center and inside: adhesion promoter
5. inside: a genuine foodstuff layer with good sealing properties as a sterilizing barrier, in order to be able to weld the film to the bottom portion of the packaging, said layer being usually made of polyethylene.

The term "flat end" refers to all of the geometric shapes that are characterized by the features that their width is less than their height and that they taper off to a point in the distal direction, when viewed in the longitudinal direction, possibly also beginning from the inside width of the cylindrical sleeve part. These shapes may be designed so as to be symmetrical or asymmetrical with respect to the longitudinal center axis.

Moreover, the invention is not limited to cylindrical sleeve parts of the packaging sleeve, but rather other cross sections of the sleeve parts may also be provided, such as, for example, a square cross section, an oval cross section or a polygonal profile, such as, for example, a hexagonal profile and so on and so forth.

Even in the case of these cross sectional shapes of the sleeve parts that are to be fitted or screwed to one another it is provided that the oppositely arranged end faces of the sleeve parts are now designed as flat ends and are integrated in vacuo in a film-like outer packaging in such a way that a formation of wrinkles in the outer packaging is avoided in the region of these end faces.

Thus, an avoidance of air pockets in the inner space of the outer packaging is avoided with a high degree of certainty; and, in addition, the formation of wrinkles is avoided, so that even the outer packaging is completely wrinkle free in this end face region of the packaging sleeve.

As a result, the service life of such an outer packaging comprising a packaging sleeve, which is enclosed air tight in said outer packaging, is significantly extended, because in the bending tests or when the end-sided ends of the outer packaging that lie now flush with one another are bent, there are no longer any wrinkles; and, therefore, there is also no longer a risk of breakage in the region of such wrinkles.

The invention is not limited to a two piece packaging sleeve with two sleeve parts that can be inserted or screwed into one another. It is also possible to provide more than two sleeve parts; and similarly it can also be provided that there is a single sleeve part, which is closed with a cover or closure that resembles a sleeve part and that is designed according to the invention.

In this case such a closure may be such that it can be screwed on or fitted on. In the case of a packaging for sterile surgical instruments and other sterile articles, it has been found to be particularly advantageous if the two sleeve parts are designed now air tight in the region of their plug or screw connection and, thus, form a first sterile barrier.

The second sterile barrier is formed by the outer vacuum packaging that is designed preferably as a tubular film that is closed by means of welding seams on its end faces.

When selecting the tubular packaging or the tubular film it is preferred that the welded ends of the tubular film can also be peeled off again from the two end faces, which means that the tubular film is provided with a coating preferably on its inside, in order to ensure when a sealing or welding seam is affixed that the sealing or welding seam can also be opened again without tearing the tubular film or damaging said tubular film in any other way.

In this way it can be ensured by affixing cut lines in the region of the end-sided ends of the outer packaging that two sheet-like film ends, which can be separated from one another, are formed; and when these film ends are pulled apart, the sealing or welding seam is split open without tearing off or ripping the film ends.

The difference between a sealing seam and a welding seam is that a sealing seam can be produced with a hot meltable adhesive or just a partial film composite between the sealed films, whereas a welding seam denotes a material formed joint between the two materials of the films, so that both materials merge and a composite is produced.

Moreover, it is provided in a preferred embodiment of the invention that the sealing or welding seam is formed on the end of the outer packaging that can be torn open such that said sealing or welding seam is formed at an approximately acute angle. That means that it is not directed transversely across the width of the outer packaging, but rather it is formed approximately in the shape of the letter A or V. That means that the first ripping movement occurs at the central tip of the sealing or welding seam, a movement that can take place with a relatively small ripping force, because this force has to be only large enough to open the tip of the A-shaped or V-shaped sealing or welding seam. Once the tip of the sealing or welding seam is opened, then the flat end of the packaging sleeve can already be pulled out merely with the hand without having to open the entire sealing or welding seam. Not until greater separating force is applied, will the legs, which are laterally connected to the tip of the A-shaped or V-shaped sealing or welding seam, be torn open, and the removal opening in the outer packaging is completely unblocked, so that the packaging sleeve can be easily removed.

In this respect it is preferred that the two conical legs of the A-shaped or V-shaped sealing or welding seam of the outer packaging in the region of the projecting end extend as far as up above the lateral surfaces of the packaging sleeve, because in this case—when the sealing or welding seam is completely torn open—a particularly good accessibility of the packaging sleeve for removal purposes is achieved.

A sterility of the inner space of the packaging sleeve is achieved preferably by a treatment with gamma rays. In a further development of the invention it is provided that both the packaging sleeve and its outer packaging are designed so as to be sterile, an aspect that is achieved by irradiating the completely finished packaging preferably with gamma rays. However, chemical reagents for producing sterility are also known and are also used here.

The subject matter of the present invention will become apparent not only from the subject matter of the individual patent claims, but also from the combination of the individual patent claims.

All of the information and features disclosed in the documents, including the abstract, in particular, the spatial design, presented in the drawings, could be claimed as essential for the invention, in so far as they are novel individually or in combination with respect to the prior art. The use of the terms "essential" or "inventive" or "essential for the invention" is subjective and does not imply that the features, which have been mentioned as such, must necessarily be an essential element of one or more patent claims.

BRIEF DESCRIPTION OF THE DRAWINGS

The invention is explained in greater detail below with reference to the drawings that depict only one way of carrying out the invention. At the same time other features, which are essential for the invention, and advantages of the invention will become apparent from the drawings and their description.

The drawings show:

FIG. 1A shows a packaging sleeve with an outer vacuum packaging in accordance with the prior art with an undesired wrinkle formation.

FIG. 1B shows a cross-section of the prior art embodiment shown in FIG. 1B.

FIG. 2A shows a packaging in an adapted tubular film in accordance with the present invention.

FIG. 2B shows a cross-section of the adapted tubular film illustrated in FIG. 2B.

FIGS. 3A-3C show various possible cross-sections of the packaging sleeve shown in FIG. 2A.

FIG. 10 shows the enlarged representation from FIG. 8, showing other details in conjunction with an improved bending behavior.

FIG. 11 shows the representation, as in FIG. 10, as both film ends are peeled open, where in this case the assistance of finger pressure for improved removal is shown.

FIG. 12 shows the position of the packaging rotated by 90 degrees, as compared to the position shown in FIG. 11.

FIGS. 13A-13D show representations of the flat ends of the packaging sleeve in a plan view, and FIGS. 13E-13H show representations of the flat ends of the packaging sleeve in cross section.

DETAILED DESCRIPTION OF THE INVENTION

Figure 4:
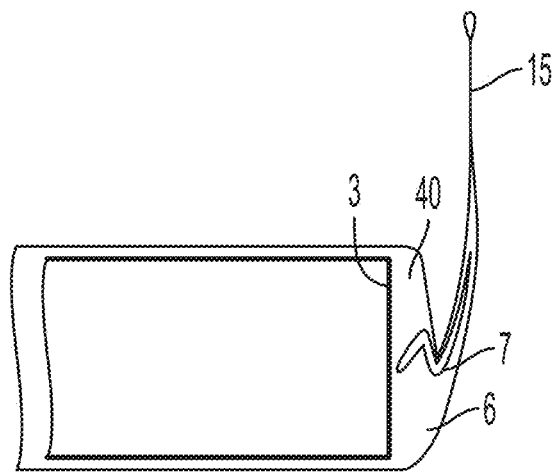
FIG. 4 shows the scaled up representation of the adjoining region between the inner packaging sleeve and the outer packaging in the end face region of the prior art.

FIG. 1 shows the prior art of a packaging sleeve, wherein the packaging sleeve is enclosed in an outer vacuum packaging.

FIG. 1 shows a round cylindrical container 1, which, however, according to FIGS. 3A-3C, could also have a cross section of any kind, for example, a round cross section, a square cross section or a polygonal cross section, as shown with the reference numerals 3, 3a and 3b, respectively.

FIG. 1 also shows in a cross section, how wrinkles 7 and air pockets 40 form in an undesired fashion, in particular, on the end faces of the container 1 when a vacuum is applied to the outer packaging 4. Said wrinkles and air pockets should be avoided, because they form predetermined breaking points in the outer packaging after prolonged use, storage or transport. Therefore, it is possible to break through the first sterility barrier.

In the exemplary embodiment according to the prior art shown in FIG. 1, the outer packaging 4 is hermetically sealed by means of upper and bottom welding seams 5.

It is shown by means of the dashed lines that it is also possible to arrange, if desired, the welding seams 33 on the longitudinal sides, so that the outer packaging 4 has to be designed, according to the prior art and according to the present invention as well, not only as a tubular film, but it may also consist of two parallel webs, which are connected lengthwise in each case by the illustrated welding seams 5, 33.

In the inner space of the container 1 there is arranged a product 2 of any kind that can be designed, according to the general description, for example, as a tool or as any other object in the form of an item (for example, also as a packaging sleeve).

It is important that the end face 3 of the container 1, according to the prior art, be planar and flat. That means that said end face does not taper off in the distal direction, but rather is designed, for example, as a round cylindrical disk or the like.

When the air is extracted from the inner space of the outer packaging, said outer packaging is supposed to nestle against the packaging sleeve, disposed in the inner space, as form-fitting and as wrinkle free as possible.

In this case an undesired transition region 6 forms in the region of the outer packaging 4; and when the air is extracted from the inner space of the outer packaging, air pockets 40 form in the region of the wrinkles 7 in said transition region.

Figure 5:
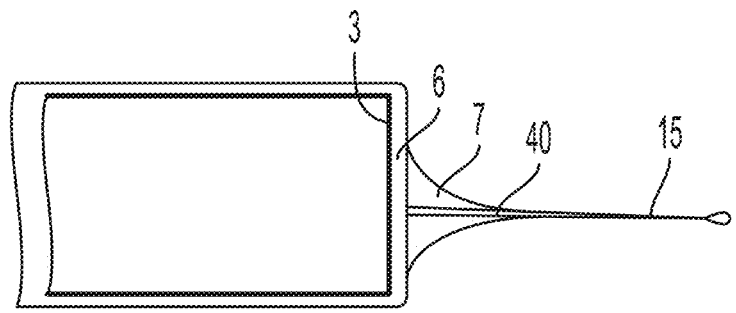
FIG. 5 shows the representation from FIG. 4 rotated by 90 degrees (as the prior art).

As a result of the layers of film in the outer packaging sticking together when the air is extracted, wrinkles 7 form in an undesired fashion in the end face region 3. These wrinkles form flexurally rigid, embrittled film regions, which then lead to breaking points in the transition region 6 when the end-sided end is bent, so that the tightness of the outer packaging ceases to exist. This aspect is shown in the lateral view in FIGS. 4 and 5, respectively, where it can be seen that, in addition to the undesired air pockets, above all, the undesired wrinkles 7 are formed, that result in the outer packaging breaking open when said wrinkles are repeatedly bent.

Figure 6:
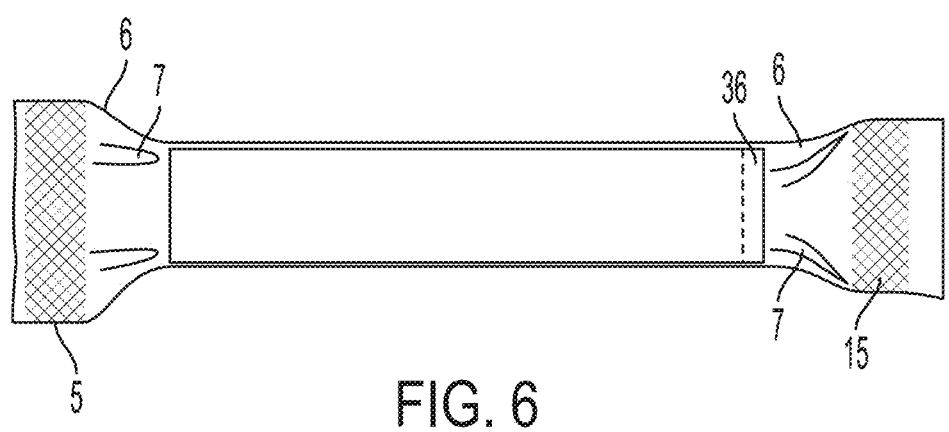
FIG. 6 shows the outer packaging, according to the prior art, with a packaging sleeve inserted into said outer packaging, with depiction of an undesired wrinkle formation.

FIG. 6 shows the same parts, as in FIG. 2, with the depiction of other details. For example, it can be provided that the container 1 is designed so as to be continuous and is closed, for example, with a cover 36; and it can be provided in another embodiment that the container 1 consists of two interconnected sleeve parts 28, 29, an aspect that will be explained in greater detail below with reference to the description of the present invention.

Figure 7:
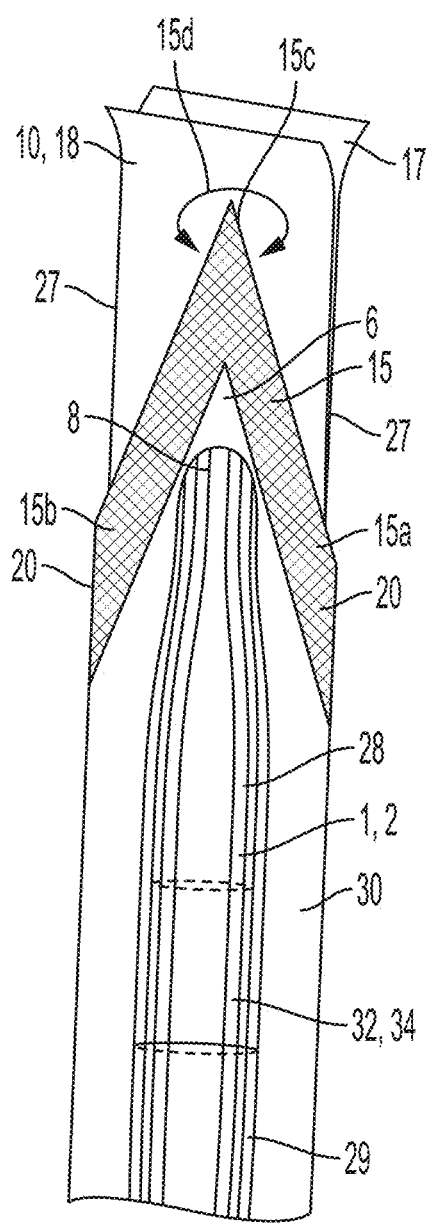
FIG. 7 shows the plan view of an inventive packaging sleeve with an outer vacuum packaging in a plan view.

FIG. 7 shows at this point the upper end of an inventive packaging sleeve with an outer vacuum packaging, where it can be seen that the container 1 now consists of two sleeve parts 28, 29, which are connected to one another in a sealed fashion by means of a plug or screw region 32 in the region of a sealing closure 34.

It is not shown that the sealing closure 34 in the region of the plug or screw region 32 can also be equipped with additional sealing measures; for example, O-ring seals can be arranged there. An adhesive bonding can also be present; or an intrinsic air-tight plug or screw connection. Similarly labels, which are glued on in a sealing fashion, may also be used in this sealing closure region, and so on and so forth.

What is important is that a sterile atmosphere is maintained in the inner space of the container 1, i.e., thus, in the inner space of the sleeve parts 28, 29, because the sealing closure 34 prevents bacteria from entering into the inner space of the sleeve parts 28, 29.

It goes without saying that it is possible in an additional embodiment that the sleeve parts 28, 29 are not designed in a mirror symmetrical identical fashion, but rather the one sleeve part 29 can be designed such that it is very long; and the other sleeve part 28 can be designed—in an axially shortened embodiment—only as a screw or plug closure in a cover-like manner.

FIG. 7 shows a specific embodiment of the inventive flat end 8, which forms the end face of the sleeve part 28.

It can be seen that the two end faces of the sleeve parts 28, 29 may be designed as the flat ends 8, 9; and it can also be only provided in another embodiment that only the end face of one sleeve part 28 or 29 may be designed as the flat end 8 or 9.

For the sake of a simpler description only one single flat end 8 on the sleeve part 28 is described in accordance with the invention. In this case it is assumed preferably, but not exclusively, that the other sleeve part 29 may also be provided with such a flat end 9.

Figure 8:
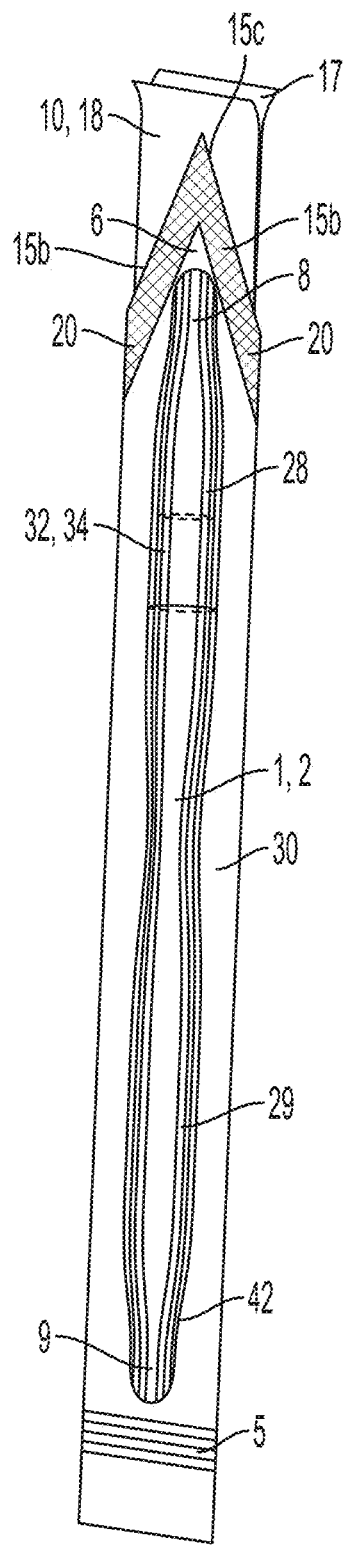
FIG. 8 shows the plan view, according to FIG. 7, with a composite representation of the packaging.

The exemplary embodiment, according to FIGS. 7 and 8, shows a particular A-shaped sealing or welding seam 15, which consists in total of two legs 15a, 15b, which run at an acute angle to each other and which converge at a central tip 15c. Said legs form an acute angle 15d, because the tubular film is then notched on the end face, in order to peel open at the illustrated cut lines 27, in order to obtain in this way two film sheets 17, 18, which can be separated from one another. What is important is that the sealing or welding seam 15 also extends as far as up to the lateral edges of the tubular film, in order to obtain in this way a tight closure on both opposite ends 20.

Thus, when the two film sheets 17, 18 are separated in the direction of the arrow 19 (see FIG. 11), the two film sheets 17, 18 can be separated from one another. The A shape of the sealing or welding seam 15 has the advantage of easy and controlled separability of both film sheets 17, 18 in the illustrated directions of the arrows 19 (see FIG. 11), because the separating force acts initially in a weaker manner on the tip 15c of the sealing or welding seam 15 and then propagates, as the ripping movement becomes stronger, into the two legs 15a, 15b, which are arranged at an angle to one another.

The reference numeral 30 denotes in general that the outer packaging 4 is designed, according to the present invention, as a tubular film 30.

However, it can also be provided in an additional embodiment that, instead of a tubular film, it is possible to use film sheets 17, 18, which run parallel to one another and which are connected to one another—straight or curved—on the longitudinal sides by means of a respective sealing or welding seam 33 (see FIG. 1).

As already stated above in the general part, the two sleeve parts 28, 29 are connected in a plug or screw region 32 and form a sealing closure 34, which ensures that the inner space of the container 1 is completely air tight with respect to the atmosphere and is closed with respect to the inner space of the outer packaging and the tubular film 30.

Moreover, it is stated in a preferred embodiment of the present invention that a necking 31 is present in the central region of the two sleeve parts 28, 29 (FIG. 9); and this necking ensures that the article, for example, a cylindrical article, such as, for example, a milling machine, a drill or a surgical instrument, which is disposed in the inner space, is better secured in position.

What is important according to the invention is that in the plan view one end face or both end faces of the two sleeve parts 28, 29 is/are designed now as flat ends 8, 9.

Figure 9:
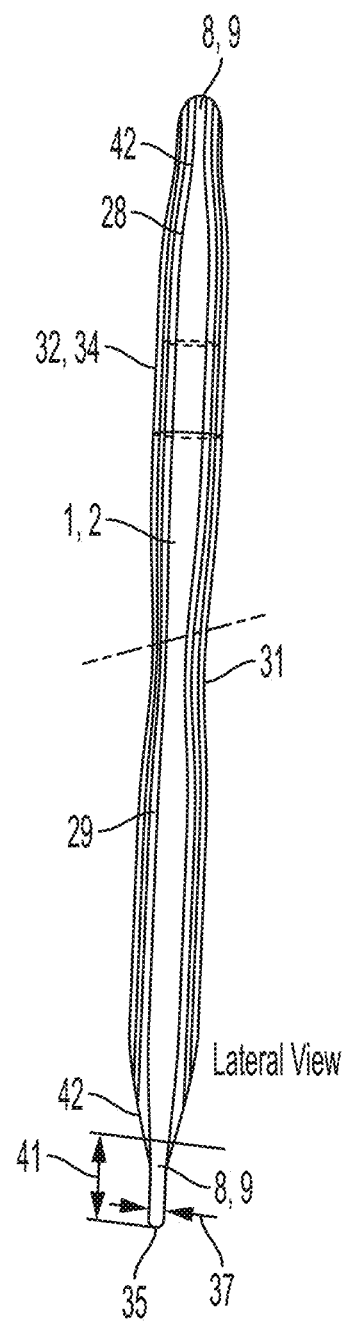
FIG. 9 shows the representation of a packaging sleeve, wherein the upper part is shown in a plan view; and the bottom part, in a lateral view.

FIG. 9 shows two representations, which are spatially rotated with respect to one another. That means that the upper part in FIG. 9 shows the flat end 8 in the lateral view, while the bottom part of the representation in FIG. 9 shows the same sleeve part in a view that is rotated by 90 degrees, where it can be seen that the flat end 8, 9 tapers off to a point in a longitudinally symmetrical fashion and has a small radius 35 at the tip.

Therefore, the width 37 of the flat end is much thinner than in comparison to the diameter of the container 1 and is about 1/10 the diameter of the container 1 in the rest of the region.

Given a container diameter 1 of, for example, 20 mm, the thickness 37 of the respective flat end 8, 9 is then only, for example, 2 mm.

As a result of the preferred blow molding method, the flat end has a wall thickness, which is larger in size—due to the method; and this wall thickness forms a penetration barrier for a tool that has sharp points and that rests on said barrier.

The axial length of the flat end can be chosen as desired. In the illustrated exemplary embodiment the flat end has, for example, a longitudinal extent of 50 mm. Preferably, a length corresponding to twice the diameter of the container 1 is chosen.

Similarly it can be provided that the length 41 of the flat end 8, 9 corresponds to about the diameter of the container 1. However, it is also possible to select the diameter in such a way that it is twice or triple the length 41.

In the exemplary embodiment according to FIG. 8, the bottom end of the tubular film 30 is also shown as a sealing or welding seam 5 that deviates from the upper sealing or welding seam 15.

Therefore, in the exemplary embodiment according to FIGS. 7 and 8, the upper sealing or welding seam 15 is provided for removing the container 1, while the bottom sealing or welding seam 5 is usually not to be opened.

FIGS. 10 and 11 show that, on account of a lack of the formation of wrinkles or the avoidance of a formation of wrinkles, bending the film region of the outer packaging in the region of a kink point 12 does not lead to a break in the outer packaging in this region, because this region no longer has any wrinkles at all.

Even in the transition region 6, which forms in the direction of the sealing or welding seam 15, there are no longer any wrinkles.

FIG. 11 shows the process, by which a mirror symmetrically designed packaging sleeve, according to FIG. 10, is removed, where it can be seen that the upper flat end 8 is designed in exactly the same way as the bottom flat end 9; and, therefore, a particularly simple removal process can take place.

If pressure is applied with the finger 22 to the bottom flat end 9 in the direction of the arrow 21, then the bottom flat end 9 in the outer packaging is pushed upwards in the direction of the arrow 24; and the upper flat end 8 can then be removed, provided that the two film sheets 17, 18 are pulled apart with the fingers of one hand in the direction of the arrow 19, so that the upper sealing or welding seam 15 is also torn open.

FIG. 12 shows a modified exemplary embodiment, where it can be seen that the upper sealing or welding seam 15a can also be designed as a transverse closure, so that the result is also film sheets 17, 18 that can be separated from one another.

It is also shown in FIG. 12 that since the flat end 9b is significantly rounded off, small wrinkles 14 are produced in an allowed manner in the bottom tubular end region 23, but said wrinkles do not have an adverse effect.

In any event what is important is that the formation of wrinkles is avoided in at least one region of the tubular film 30, i.e., thus, in the region of the upper flat end 8 and/or in the region of the bottom flat end 9.

However, the avoidance of a formation of wrinkles on both the upper and also the bottom side of the tubular film 30 is not always automatically necessary.

FIGS. 13A-H show various design shapes of flat ends, where FIGS. 13A-D show the lateral view of various embodiments of flat ends 8, 9, while FIGS. 13E-H show the associated end views of these flat ends 8, 9.

It is still specified that the flat ends form in each case tips 38, 39, so that the plan view of the tips 38, 39 in the various embodiments is also shown in the bottom representation.

Therefore, the first column (FIGS. 13A, 13E) shows a tip 38a, 38b, which tapers off such that it is relatively pointed, and the flat end is designed so as to be approximately square and tapers (42a), therefore, into the tip 38a, 38b. The second column (FIGS. 13B, 13F) shows that the flat end 8b, 9b ends such that it is rounded off approximately in the shape of a beak (42*b*); and the plan view also shows a tip 38*b*, 39*b* that is reduced with respect to the diameter of the container 1.

The third column (FIGS. 13C, 13G) shows a relatively acute angled embodiment of the flat end 8*c*, 9*c*; and the associated tips 38*c* and 39*c* extend exactly symmetrically, but start from an oval cross section (42*c*).

In the right column (FIGS. 13D, 13H) the tip 38*d*, 39*d* is pointed even more and ends, moreover, in an approximately oval cross section (42*d*). Such a cross sectional shape has been found in tests to be an optimal solution.

Figure 14:
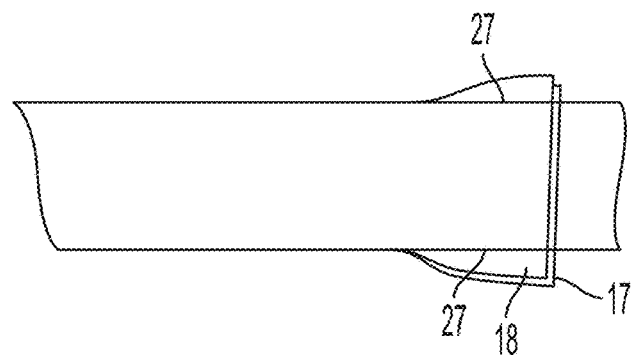
FIG. 14 shows the representation of the tubular film with the cut lines being affixed for purposes of an improved peeling open.

FIG. 14 shows the peeling open process that is shown in FIG. 11, where it can be seen that the film tube can be torn open along the cut lines 27.

Figure 15:
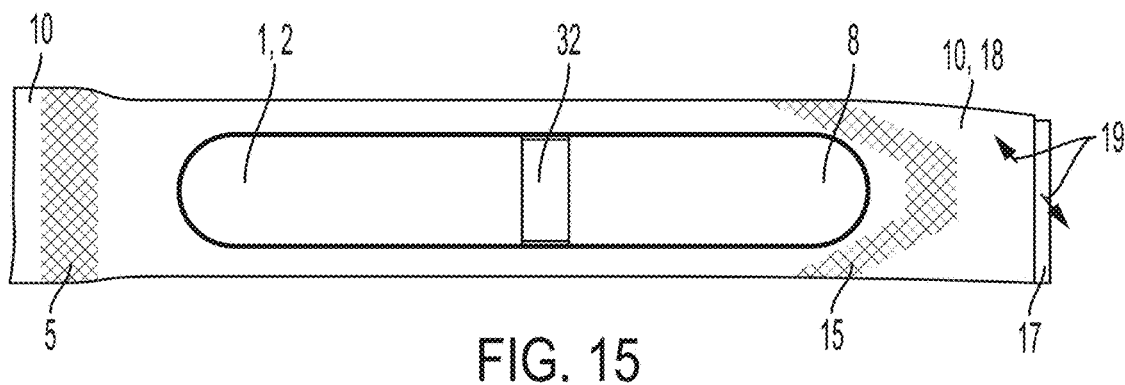
FIG. 15 shows an exemplary embodiment of a packaging sleeve with an outer vacuum packaging with the end of the film being peeled open.
Figure 16:
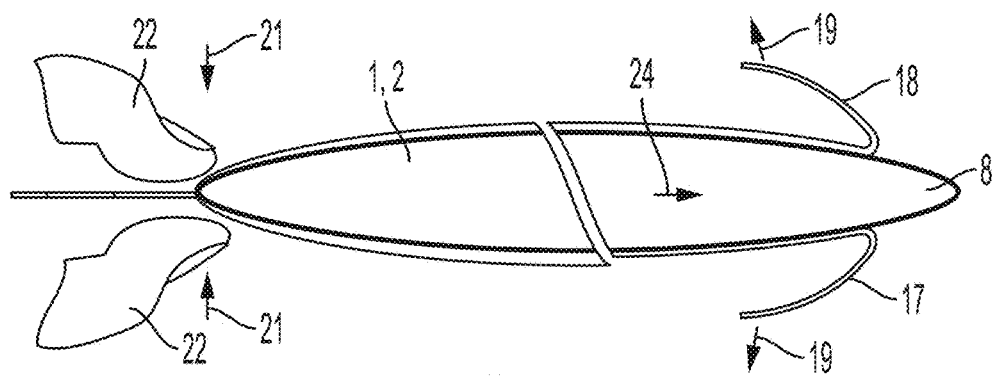
FIG. 16 shows the advancing unpacking of the packaging sleeve, according to FIG. 15, as the packaging sleeve is squeezed out of the outer packaging.

FIGS. 15 and 16 show a process for removing a container 1 with a product 2, enclosed therein, of the kind that has already been explained above with reference to FIG. 11. In this case the plan view is shown in FIG. 15; and the lateral view is shown in FIG. 16.

Figure 17:
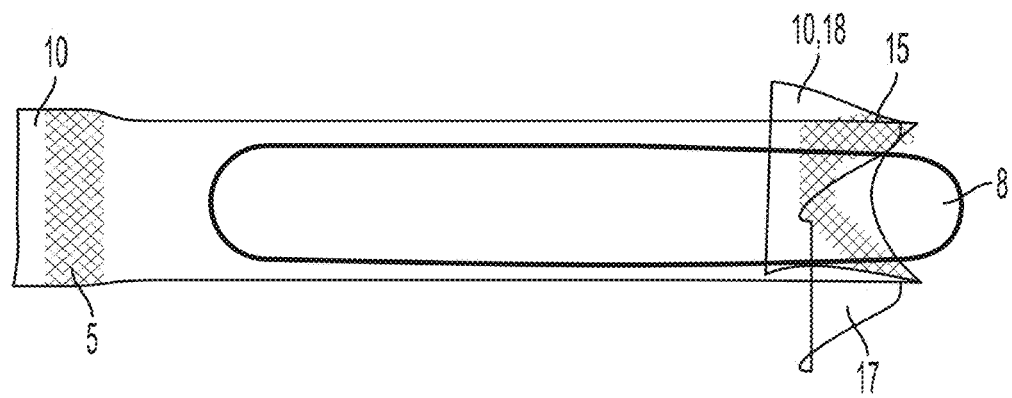
FIG. 17 shows the representation rotated by 90 degrees, as compared to FIG. 16.

FIG. 17 shows the almost completed removal position, so that now with the film sheets 17, 18 having been peeled off, the upper flat end 8 can be removed.

Figure 18:
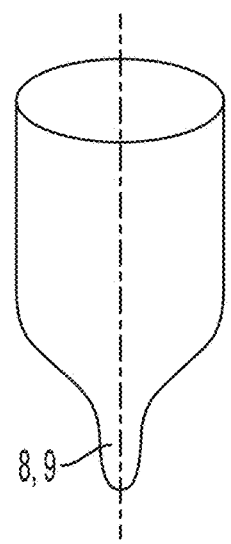
FIG. 18 shows the lateral view of a flat end in a symmetrical design.
Figure 19:
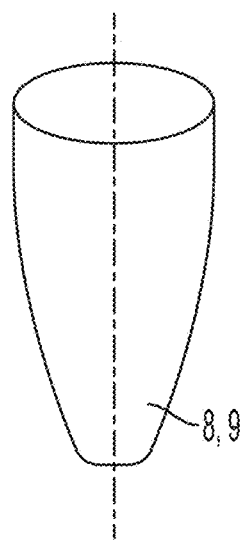
FIG. 19 shows the plan view of an embodiment, rotated by 90 degrees, according to FIG. 18.
Figure 20:
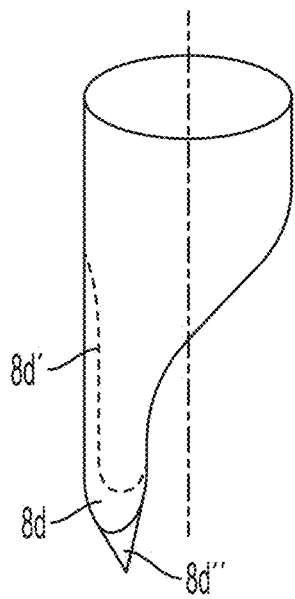
FIG. 20 shows the lateral view of an asymmetrical flat end in three different embodiments.
Figure 21:
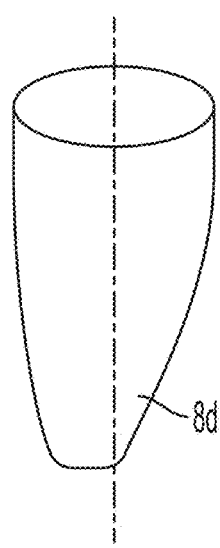
FIG. 21 shows the plan view of the representation, rotated by 90 degrees, according to FIG. 20, in only one embodiment.

FIGS. 18 and 19 show in conformity with the previous exemplary embodiments a mirror symmetrical configuration of the flat ends 8, 9 in a lateral view and a plan view, while FIGS. 20 and 21 show different embodiments of asymmetrically designed flat ends.

FIG. 20 shows an asymmetrical flat end 8*d*, which is designed so as to be eccentric to the longitudinal center axis; and this flat end 8*d* can also take accordingly a shape 8*d'* or a shape 8*d"*.

Figure 22:
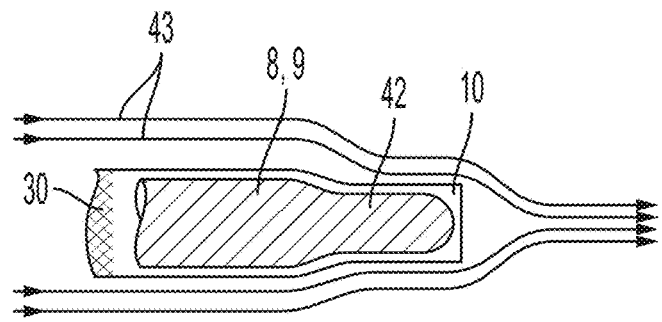
FIG. 22 shows representation of the streamlined transition profile of the packaging sleeve.

FIG. 22 shows a drawing of the underlying principle, how a body, around which (gaseous or liquid) streamlines 43 flow, in the form of the packaging sleeve of the invention forms the transition profile 42. It can be seen that the transition profile 42 at the end faces of the packaging sleeve corresponds approximately to a streamline 43. That means that there is a continuous and harmonic transition from the larger cross section of the packaging sleeve in the center region into the flattened end face of the packaging sleeve in the manner of a streamline.

| List of Reference Numerals | |
|---|---|
| 1 | container |
| 2 | product |
| 3 | end face |
| 4 | outer packaging |
| 5 | sealing or welding seam (at the bottom) |
| 6 | transition region |
| 7 | wrinkle |
| 8 | flat end a, b, c, d |
| 9 | flat end a, b, c, d |
| 10 | projecting end |
| 11 | welding seam |
| 12 | kink point |
| 13 | adjoining region |
| 14 | wrinkle |
| 15 | sealing or welding seam (tip) |
| 15a | leg |
| 15b | leg |
| 15c | tip |
| 15d | wrinkle |
| 16 | curved seam |
| 17 | film sheet |
| 18 | film sheet |
| 19 | direction of arrow |
| 20 | end (of 15) |
| 21 | direction of arrow |

-continued

| List of Reference Numerals | |
|---|---|
| 22 | finger |
| 23 | tubular end |
| 24 | direction of arrow |
| 25 | cut line |
| 26 | finger surface |
| 27 | cut line |
| 28 | sleeve part |
| 29 | sleeve part |
| 30 | tubular film |
| 31 | necking |
| 32 | plug or screw region |
| 33 | welding seam (prior art) |
| 34 | sealing closure |
| 35 | radius |
| 36 | cover |
| 37 | thickness |
| 38 | tip a, b, c, d |
| 39 | tip a, b, c, d |
| 40 | air pocket |
| 41 | length |
| 42 | transition profile (streamlined) |
| 43 | streamline |

What is claimed is:

1. A medical packaging for the sterile storage of medical articles in a hermetically sealable, sterile packaging sleeve, the packaging comprising:

a packaging sleeve having at least two sleeve parts connectable to form an air tight seal to contain a medical article therein, the packaging sleeve having opposite end face regions, wherein each of the end face regions form a streamlined profile which tapers from a larger periphery of the packaging sleeve to an end that is reduced in thickness and rounded, and wherein the end of at least one of the end face regions is shaped as a beak or a pointed cone; and a film-like outer packaging that encloses the packaging sleeve, wherein the outer packaging comprises at least one end sealed with a sealing or welding seam, and wherein the outer packaging has a negative pressure with respect to atmospheric pressure, and as a result, the outer packaging surrounds the packaging sleeve on all sides in a form-fitting manner, wherein a length of the outer packaging is longer than a length of the packaging sleeve so that the outer packaging projects beyond the end face regions of the packaging sleeve to form projecting lengths, wherein the sealing or welding seam is arranged in at least one of the projecting lengths of the outer packaging adjacent the end face region of the packaging sleeve to form a sealed projecting length, and wherein the sealed projecting length of the outer packaging is configured to achieve a continuous transition from the end face region of the packaging sleeve to the sealing or welding seam so that it remains substantially wrinkle free when surrounding the packaging sleeve in the form-fitting manner under the negative pressure.

2. The medical packaging of claim 1, wherein the packaging sleeve comprises an approximately cylindrical cross section, and the streamlined profile of at least one end face region is flattened off perpendicular to a width of the packaging sleeve.

3. The medical packaging of claim 1, wherein the streamlined profile of the at least one end face region shaped as the beak comprises a width approximately equal to a diameter of the cylindrical packaging sleeve.

4. The medical packaging of claim 1, wherein the at least two sleeve parts of the packaging sleeve are connectable to one another in a sealing fashion with a screw connection.

5. The medical packaging of claim 1, wherein the at least two sleeve parts of the packaging sleeve are connectable to one another in a sealing fashion by sliding one packaging part onto the other packaging.

6. The medical packaging of claim 1, wherein the outer packaging can be peeled open on the at least one end comprising the sealing or welding seam.

7. The medical packaging of claim 6, wherein the sealing or welding seam is formed at an approximately acute angle in the manner of a V shape.

8. The medical packaging of claim 1, wherein the outer packaging comprises two ends sealed with a sealing or welding seam, wherein the outer packaging can be peeled open on one or both of the sealing or welding seams.

9. The medical packaging of claim 8, wherein one of the sealing or welding seams is formed at an approximately acute angle in the manner of a V shape.

10. The medical packaging of claim 2, wherein the at least one end face region that is flattened off is mirror symmetrical to a longitudinal center axis of the packaging sleeve.

11. The medical packaging of claim 2, wherein the at least one end face region that is flattened off is asymmetrical to the longitudinal center axis of the packaging sleeve.

12. The medical packaging of claim 2, wherein an axial length of the at least one end face region that is flattened off corresponds to approximately twice a diameter of the packaging sleeve.

13. The medical packaging of claim 2, wherein a thickness of a distal tip of the at least one end face region that is flattened off corresponds to approximately 1/10 a diameter of the packaging sleeve.

14. The medical packaging of claim 2, wherein the at least one end face region that is flattened off comprises a linear longitudinal extent.

15. The medical packaging of claim 2, wherein the at least one end face region that is flattened off comprises a curved longitudinal extent having a spoon shape.

16. The medical packaging of claim 1, wherein at least an inner space of the packaging sleeve is sterile.

17. The medical packaging of claim 1, wherein the negative pressure of the outer packaging forms a vacuum intermediate space between the outer packaging and the packaging sleeve, wherein the vacuum intermediate space is sterile.

18. The medical packaging of claim 1, wherein the streamlined profile of at least one end face region is flattened off perpendicular to a width of the packaging sleeve and tapers into a curved end.

19. A medical packaging for the sterile storage of medical articles in a hermetically sealable, sterile packaging sleeve, the packaging comprising:
a packaging sleeve having at least two sleeve parts connectable to form an airtight seal to contain a medical article therein, the packaging sleeve having:
a necking in a central region of the at least two sleeve parts to better secure the medical device in position, and
opposite end face regions having a streamlined profile that tapers from a larger periphery of the packaging sleeve to an end that is reduced in thickness and rounded; and
a film-like outer packaging that encloses the packaging sleeve in a form-fitting manner, wherein the outer packaging comprises at least one end sealed with a sealing or welding seam, and wherein the outer packaging has a negative pressure with respect to atmospheric pressure,
wherein a length of the outer packaging is longer than a length of the packaging sleeve so that the outer packaging projects beyond the end face regions of the packaging sleeve to form projecting lengths,
wherein the sealing or welding seam is arranged in at least one of the projecting lengths of the outer packaging adjacent the end face region of the packaging sleeve to form a sealed projecting length, and
wherein the sealed projecting length of the outer packaging is configured to achieve a continuous transition from the end face region of the packaging sleeve to the sealing or welding seam so that it remains substantially wrinkle free when surrounding the packaging sleeve in the form-fitting manner under the negative pressure.

20. The medical packaging of claim 19, wherein the streamlined profile of at least one end face region is flattened off perpendicular to a width of the packaging sleeve and tapers into a curved end.

* * * * *